United States Patent
O'Malley et al.

(10) Patent No.: US 9,981,080 B2
(45) Date of Patent: May 29, 2018

(54) DISPOSABLE WOUND IRRIGATION DEVICE AND ASSOCIATED METHOD OF USE

(71) Applicant: Centurion Medical Products Corporation, Williamston, MI (US)

(72) Inventors: Patrick Martin O'Malley, Chapin, SC (US); Michael David Horning, Irmo, SC (US)

(73) Assignee: Centurion Medical Products Corporation, Williamston, MI (US)

( * ) Notice: Subject to any disclaimer, the term of this patent is extended or adjusted under 35 U.S.C. 154(b) by 965 days.

(21) Appl. No.: 14/455,364

(22) Filed: Aug. 8, 2014

(65) Prior Publication Data

US 2015/0045750 A1 Feb. 12, 2015

Related U.S. Application Data

(60) Provisional application No. 61/864,096, filed on Aug. 9, 2013, provisional application No. 61/869,819, filed on Aug. 26, 2013.

(51) Int. Cl.
*A61M 3/00* (2006.01)
*A61M 35/00* (2006.01)
*A61M 3/02* (2006.01)

(52) U.S. Cl.
CPC ....... *A61M 3/0237* (2013.01); *A61M 2210/04* (2013.01)

(58) Field of Classification Search
CPC ............................ A61M 35/00; A61M 3/0233
See application file for complete search history.

(56) References Cited

U.S. PATENT DOCUMENTS

| 790,318 | A | * | 5/1905 | Sams | B05B 7/2429 128/200.14 |
|---|---|---|---|---|---|
| 2,524,720 | A | * | 10/1950 | Watrous | A61F 9/0008 528/26 |

(Continued)

OTHER PUBLICATIONS

PCT International Preliminary Report on Patentability and Written Opinion dated Feb. 14, 2017 for PCT/US2015/014177.

(Continued)

*Primary Examiner* — Susan Su
(74) *Attorney, Agent, or Firm* — Kristin L. Murphy; Brooks Kushman P.C.

(57) ABSTRACT

A wound irrigation device, comprising: a cap structure configured to engage a bottle containing an irrigation solution at a first end; a protective rim disposed about a periphery of the cap structure at a second end, wherein the protective rim is selectively disposed about or in proximity to a wound to be irrigated when in use; one or more conduits for selectively communicating a compressed gas through the cap structure and into an interior of the bottle to form a compressed irrigation solution; and a longitudinal wall structure disposed within the cap structure and defining one or more channels for selectively communicating the compressed irrigation solution through the cap structure and to the wound. The wound irrigation device further comprising a vent conduit in fluid communication with the one or more conduits for selectively venting the compressed gas through the cap structure and into the environment.

18 Claims, 2 Drawing Sheets

(56) References Cited

U.S. PATENT DOCUMENTS

| | | | |
|---|---|---|---|
| 3,261,355 A * | 7/1966 | Burbig | A61H 35/02 604/296 |
| 4,093,124 A * | 6/1978 | Morane | A61M 11/02 128/200.14 |
| 4,131,115 A * | 12/1978 | Peng | A61H 35/02 604/297 |
| 5,059,187 A * | 10/1991 | Sperry | A61M 3/0237 128/200.23 |
| 5,133,701 A * | 7/1992 | Han | A61M 3/0233 128/200.23 |
| 5,242,422 A | 9/1993 | Schneberger et al. | |
| 5,441,174 A * | 8/1995 | Sperry | A61M 3/0287 222/105 |
| 5,795,324 A | 8/1998 | Morse | |
| 5,830,197 A | 11/1998 | Rucinski | |
| 5,860,947 A | 1/1999 | Stamler | |
| 6,050,981 A | 4/2000 | Lampropoulos et al. | |
| 6,125,843 A * | 10/2000 | Gold | A61M 3/0275 128/200.23 |
| 6,210,381 B1 * | 4/2001 | Morse | A61M 3/0279 604/289 |
| 6,468,253 B1 * | 10/2002 | Rucinski | A61M 3/02 128/898 |
| 6,485,452 B1 | 11/2002 | French et al. | |
| 6,878,142 B2 | 4/2005 | Lawrence et al. | |
| D556,595 S | 12/2007 | Rucinski | |
| D588,692 S | 3/2009 | Rucinski | |
| 7,540,860 B2 | 6/2009 | Stamler | |
| 7,662,125 B2 | 2/2010 | Rucinski | |
| 8,002,757 B1 | 8/2011 | Schultz | |
| 8,021,346 B2 | 9/2011 | Rucinski | |
| 8,241,259 B2 | 8/2012 | Rucinski | |
| 8,747,372 B1 | 6/2014 | Schultz | |
| 2004/0116903 A1 | 6/2004 | Osman | |
| 2005/0124946 A1 | 6/2005 | Landau et al. | |
| 2005/0148958 A1 * | 7/2005 | Rucinski | A61M 3/02 604/290 |
| 2007/0055208 A1 * | 3/2007 | Berger | A61F 9/0026 604/295 |
| 2010/0121261 A1 * | 5/2010 | Kablik | A61K 31/74 604/58 |
| 2012/0035559 A1 | 2/2012 | Rucinski | |
| 2013/0190698 A1 | 7/2013 | Carson | |

OTHER PUBLICATIONS

May 14, 2015 International Search Report issued in International Patent Application No. PCT/US15/14177.

* cited by examiner

DISPOSABLE WOUND IRRIGATION DEVICE AND ASSOCIATED METHOD OF USE

CROSS-REFERENCE TO RELATED APPLICATIONS

The present patent application/patent claims the benefit of priority of U.S. Provisional Patent Application No. 61/864,096, filed on Aug. 9, 2013, and entitled "DISPOSABLE WOUND IRRIGATION DEVICE" and U.S. Provisional Patent Application No. 61/869,819, filed on Aug. 26, 2013, and entitled "WOUND IRRIGATION DEVICE," the contents of both of which are incorporated in full by reference herein.

FIELD OF THE INVENTION

The present invention relates generally to the medical device field. More specifically, the present invention relates to a disposable wound irrigation device and an associated method of use.

BACKGROUND OF THE INVENTION

In the medical setting, the necessity of adequately cleansing a wound is critical in reducing the level of bacteria and particulate matter in and around the wound. To this end, numerous conventional devices have been developed for irrigating a wound with an aqueous solution, some of which are wholly or partially disposable, and some of which incorporate a splash shield or the like. However, most of these conventional devices operate by a user manipulating the device in some manner, e.g. by squeezing it or pulling a trigger.

For example, U.S. Patent Application No. 2013/0190698 (Carson) provides a device for the irrigation of wounds, wherein the device comprises: a port for the attachment an oxygen supply, an area that sealably attaches to a supply of sterile saline, and a tube portion, wherein sterile saline may be sent through the tube portion and out of a nozzle, wherein the nozzle may be directed to irrigate a wound. In certain embodiments, the invention further comprises a device wherein the tube portion and nozzle permit sterile saline to be moved out of the nozzle at a pressure of 5 to 8 psi. In certain embodiments, the invention further comprises a device wherein the tube portion and nozzle permit sterile saline to be moved out of the nozzle at a pressure of 7 to 8 psi. In certain embodiments, the device further comprises a means to modulate the pressure of sterile saline flowing through the nozzle. In certain embodiments, the invention further comprises a device wherein the area that sealably attaches to a supply of sterile saline is an aperture with internal threads, wherein the internal threads are capable of screwing onto a bottle of commercially available medical grade saline. In certain embodiments, the device which further comprises a mechanism which allows an operator to easily turn the flow of sterile saline on and off. In certain embodiments, the mechanism comprises a trigger. Finally, in certain embodiments, the invention further comprises a device wherein the port attaches to a pressurized oxygen supply.

U.S. Pat. No. 8,241,259 (Rucinski) provides a novel and inexpensive method and device for convenient and effective manual wound irrigation. In one embodiment, the subject invention provides a discharge means for a standard reservoir housing containing an adequate volume of irrigation solution wherein the discharge means has a plurality of nozzles through which the irrigation solution can pass. In a preferred embodiment, the reservoir housing, upon which the discharge means is affixed, is compressible or squeezable (e.g. plastic bottles in which the saline solutions are presently available). The medical or health care professional or other person using the subject device and providing wound irrigation therapy can compress the reservoir housing to force the irrigation solution through the nozzles under sufficient pressure to dislodge dirt, debris, or other particles, including microorganisms, e.g. pathogenic bacteria. In another embodiment, elongated ports are used to achieve the desired dispersal of the stream of irrigation solution. The object of this invention is to provide an easy to use, economical wound irrigation method and device which are capable of delivering adequate volumes of irrigation solution (without refilling the reservoir) in a dispersed stream under sufficient pressure to effectively cleanse the wound thereby reducing the incidence of infection. The invention would allow the medical professional to, without assistance, easily direct and control the application of irrigation solution with one hand, leaving the other hand free for other activities such as separation of the wound to further facilitate irrigation.

U.S. Pat. No. 7,540,860 (Stamler) provides a splashback shield for attachment to a syringe for wound irrigation that includes a generally dome-shaped shield with a conduit or tunnel through the top that narrows to form a nozzle as it extends substantially inside the shield. A number of air vents or passageways surround the conduit so when submerging and re-filling the syringe with irrigant with the shield attached any air trapped inside the shield escapes rather than drawn into the syringe. The air vents are preferably elongate tubular passageways that narrow exiting the shield, facilitating air escaping but the irrigant mixed with any blood and contamination tends not to pass through the vents. The device is an improvement over conventional products.

U.S. Pat. No. 6,878,142 (Lawrence, et al.) provides an improved suction and irrigation system for debriding a tract wound that includes a suction and irrigation handpiece and a dual lumen suction and irrigation tip that is removably connectible to the handpiece. The tip has a flexible shaft and a connector for connecting the shaft to the handpiece. The flexibility of the shaft facilitates advancement of the shaft to the deepest part of the tract wound while also limiting further trauma to the wound. Likewise, U.S. Pat. No. 6,485,452 (French, et al.) provides a medical suction and irrigation apparatus that includes a suction/irrigation tip removably connected to a conventional suction/irrigation handpiece. Suction is provided through a suction tube which has a bypass conduit in the tip. The bypass conduit is directly connectable to a suction source so that aspirated debris passes through the tip to the suction source. The suction tube thus prevents aspirated debris from entering the conventional suction tube in the handpiece and contaminating the handpiece. The suction tube is also designed to have a maximum size to prevent the tip from clogging. The tip also has an irrigation tube for directing irrigation liquid to the irrigation site, and a connector which connects the irrigation tube to the handpiece so that the handpiece pumps fluid through the tip in a conventional manner. A flexible splash shield, slidably mounted to the irrigation tube, confines irrigation fluid to the local site.

Finally, U.S. Pat. No. 6,050,981 (Lampropoulos, et al.) provides a system for irrigating a wound with wound irrigation fluid and for preventing substantial splashback of the wound irrigation fluid. The system comprises: (i) a fluid delivery device for delivering wound irrigation fluid; and (ii) a flexible wound irrigation shield configured such that the shield prevents substantial splashback of the irrigation fluid upon irrigation of a wound. The shield is configured to be disposed, preferably removably, on the fluid delivery device. The flexible shield is substantially conformable to a desired wound area, enabling the practitioner to irrigate awkward, uneven, and hard to reach areas. The shield can be folded into a compact position, then opened into a larger shield. The fluid delivery device comprises (i) a fluid source for providing wound irrigation fluid; and (ii) an adaptor for transmitting fluid from the fluid source to the wound. In one embodiment, the adaptor has a substantially planar face that is substantially coplanar with the plane defined by the shield, thereby preventing patient puncture. The preferred adaptor, preferably a multi-part adaptor, features spray pattern adjustability, removable coupling to the shield, the capacity for removably coupling to a variety of different fluid sources, and a variety of other features and advantages.

Thus, what is still needed in the art is an improved disposable wound irrigation device.

BRIEF SUMMARY OF THE INVENTION

In one exemplary embodiment, the present invention provides a wound irrigation device, comprising: a cap structure configured to engage a bottle containing an irrigation solution at a first end; a protective rim disposed about a periphery of the cap structure at a second end opposite the first end, wherein the protective rim is selectively disposed about or in proximity to a wound to be irrigated when in use; one or more conduits for selectively communicating a compressed gas through the cap structure and into an interior of the bottle containing the irrigation solution to form a compressed irrigation solution; and a longitudinal wall structure disposed within the cap structure and defining one or more channels there through for selectively communicating the compressed irrigation solution through the cap structure and to the wound to be irrigated. The wound irrigation device further comprises a vent conduit in fluid communication with the one or more conduits for selectively venting the compressed gas through the cap structure and to an external environment. The vent conduit exits the cap structure coincident to one of a recess and a protrusion manufactured into an exterior surface of the cap structure. The cap structure comprises a circumferential wall structure disposed about the longitudinal wall structure. The cap structure further comprises a plurality of friction structures disposed about an external surface of the circumferential wall structure. The protective rim defines one or more recesses along an outer edge thereof through which the compressed irrigation solution, debris, blood, and infectious particles egress from the vicinity of the wound. Optionally, the wound irrigation device further comprises one or more backflow prevention valves disposed along the one or more conduits. Optionally, the wound irrigation device further comprises a flow regulator disposed along the one or more conduits. The one or more conduits are selectively coupled to a compressed gas source.

In another exemplary embodiment, the present invention provides a method for using a wound irrigation device, comprising: attaching a wound irrigation device to a bottle containing an irrigation solution, the wound irrigation device comprising: a cap structure configured to engage the bottle containing the irrigation solution at a first end; a protective rim disposed about a periphery of the cap structure at a second end opposite the first end, wherein the protective rim is selectively disposed about or in proximity to a wound to be irrigated when in use; one or more conduits for selectively communicating a compressed gas through the cap structure and into an interior of the bottle containing the irrigation solution to form a compressed irrigation solution; and a longitudinal wall structure disposed within the cap structure and defining one or more channels there through for selectively communicating the compressed irrigation solution through the cap structure and to the wound to be irrigated; coupling the one or more conduits of the wound irrigation device to a compressed gas source; inverting the bottle containing the irrigation solution over the wound to be irrigated with the protective rim one of in contact with and at a predetermined distance from the wound to be irrigated; and actuating the wound irrigation device such that the compressed gas flows into the bottle containing the irrigation solution and forces irrigation solution onto the wound to be irrigated through the one or more channels. The method further comprises actuating the wound irrigation device by obstructing a vent conduit in fluid communication with the one or more conduits, the vent conduit for selectively venting the compressed gas through the cap structure and to an external environment. The vent conduit exits the cap structure coincident to one of a recess and a protrusion manufactured into an exterior surface of the cap structure. The cap structure comprises a circumferential wall structure disposed about the longitudinal wall structure. The cap structure further comprises a plurality of friction structures disposed about an external surface of the circumferential wall structure. The protective rim defines one or more recesses along an outer edge thereof through which the compressed irrigation solution, debris, blood, and infectious particles egress from the vicinity of the wound. Optionally, the wound irrigation device further comprises one or more backflow prevention valves disposed along the one or more conduits. Optionally, the wound irrigation device further comprises a flow regulator disposed along the one or more conduits.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
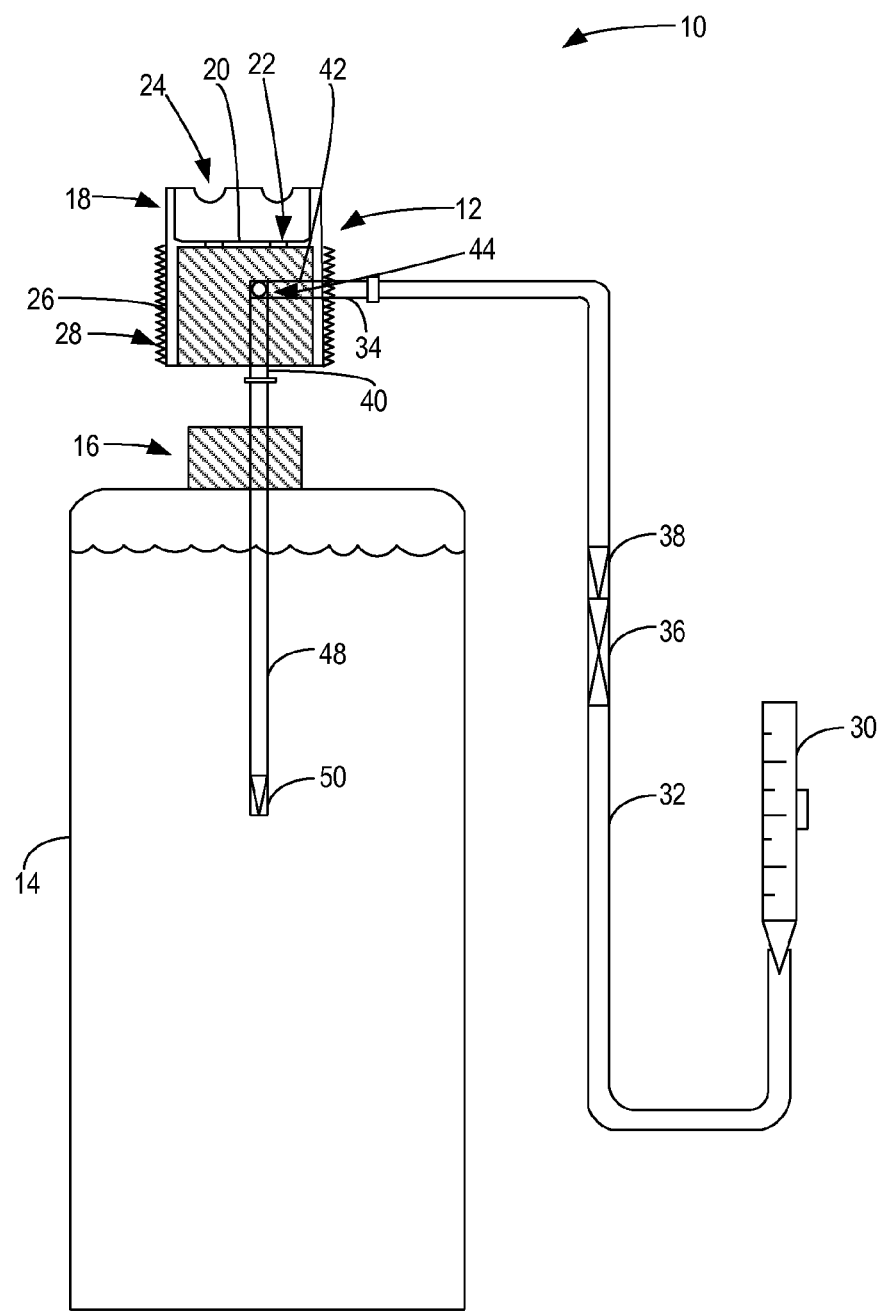
FIG. 1 is a schematic diagram illustrating one exemplary embodiment of the wound irrigation device of the present invention, as attached to a conventional saline bottle.
Figure 2:
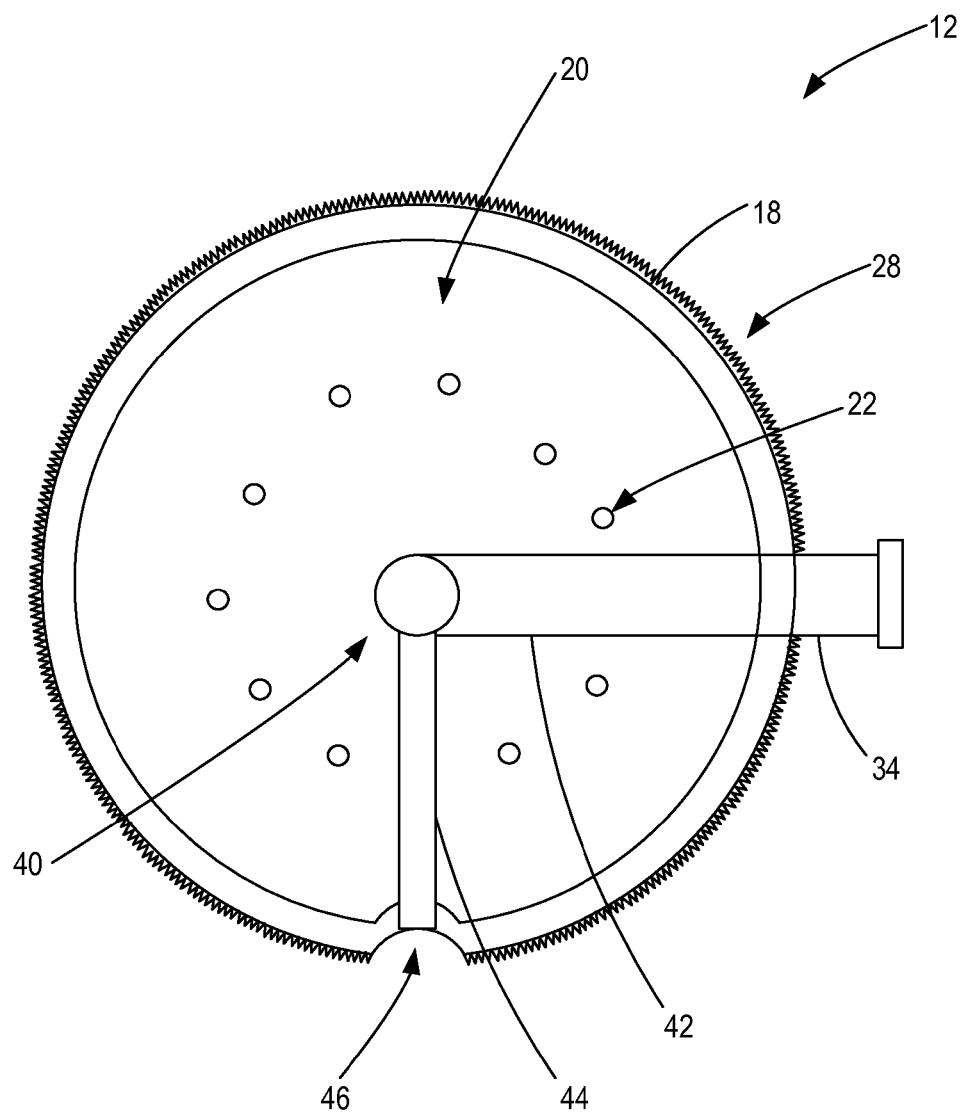
FIG. 2 is another schematic diagram illustrating one exemplary embodiment of the wound irrigation device of the present invention.

Referring now specifically to FIGS. 1 and 2, in one exemplary embodiment, the wound irrigation device 10 of the present invention includes a cap 12 that screws onto or otherwise attaches to an industry standard bottle 14 of normal saline, sterile water, or the like via a conventional thread set 16 or the like. Such industry standard bottles of normal saline, sterile water, or the like are widely used for the irrigation of wounds. Accordingly, the cap 12 and all other components of the wound irrigation device 10 described herein may be manufactured from any medically compatible materials, such as medically compatible metals, plastics, polymers, etc.

The cap 12 includes several components. When attached to the bottle 14, the cap includes a free end that has a protective rim 18 that serves as a splash shield. When the bottle 14 is inverted over a wound to deliver a pressurized aqueous solution to the wound, at a minimum, the protective rim 18 holds the longitudinal wall 20 of the cap 12 and channels 22 for delivering the pressurized aqueous solution to the wound a predetermined distance away from the wound, while generally localizing the pressurized aqueous solution to the area of the wound and potentially protecting the user and surrounding equipment from undesirable exposure to splashed irrigation solution, debris, blood, and infectious particles from the vicinity of the wound.

The protective rim 18 of the cap 12 may be substantially transparent, such that the would may be visualized during irrigation, and may include any number of small recesses 24 disposed along its free end that allow for the controlled egress of irrigation solution, debris, blood, and infectious particles from the vicinity of the wound during irrigation.

The bulk of the cap 12 includes a circumferential wall 26 that, preferably, includes one or more friction surfaces 28, in any conventional configuration, for assisting the user in screwing the cap 12 onto or off of the bottle 14. Accordingly, the one or more friction surfaces 28 may be manufactured into the exterior surface of the circumferential wall 26 or may be mechanically achieved subsequent to manufacturing. In general, the circumferential wall 26 and the protective rim 18 define a substantially cylindrical hollow cap 12 that may be screwed onto a bottle 14 and provide an irrigation solution delivery space substantially adjacent to a wound, with the longitudinal wall 20 defining two distinct chambers. The longitudinal wall 20 may have any suitable thickness and may be integrally formed with other adjacent components of the wound irrigation device 10.

The cap 12 may rely on conventional threading associated with a variety of standard saline bottles. The threads of the cap 12 may be mechanically introduced into the interior surface of the cap 12 during the manufacturing process so as to fit securely with a variety of different bottle types and thread designs. Alternatively, a soft rubber gasket may be disposed on the interior surface of the cap 12 that may allow the cap 12 to "self thread" onto the bottle, thereby allowing it to be used on a wide variety of bottle and thread types and still create a seal to prevent accidental leakage of saline and ensure a tight seal.

The channels 22 in the longitudinal wall 20 of the cap 12 may be in any number, any size, and have any configuration suitable for allowing the pressurized aqueous solution to be communicated from the interior of the bottle 14, through the cap 12, and to the wound to be irrigated. Advantageously, the number, size, and configuration of the channels may be used to achieve desired pressure and fluid delivery characteristics, much as a nozzle would be used.

The cap 12 is connected to an external compressed gas source 30, such as a compressed air source or a compressed oxygen source, both widely used in the healthcare setting in the form of a wall mounted or portable unit or canister. The compressed gas source 30 is coupled to the cap 12 via flexible tubing 32 or the like that selectively engages an inlet port 34 manufactured into or disposed in the cap 12, such as via a barb, a hub connector, a threaded connector, a luer-lock mechanism, etc. A similar methodology may be used to connect the flexible tubing 32 to the compressed gas source 30. It will be readily apparent to those of ordinary skill in the art that the flexible tubing 32 may also include one or more substantially rigid portions, if so desired. Optionally, the flexible tubing 32 may include a flow regulator 36 for regulating the flow of compressed gas through the flexible tubing 32 and into the bottle 14 and/or a backflow prevention valve 38 for preventing backflow of the compressed gas and/or aqueous solution from the bottle 14 into the compressed gas source 30. Such regulators and valves are well known to those of ordinary skill in the art and are widely used in the healthcare industry.

The inlet port 34 disposed through the circumferential wall 26 is coupled to an outlet port 40 at the threaded end of the cap 12 via an elbow 42 or other conduit. The elbow 42 or other conduit preferably includes a vent port 44 that passes through the circumferential wall 26 separate from the inlet port, exiting the cap 12 within a recess 46, protrusion, or the like manufactured into the exterior thereof, thereby enabling tactile location of the vent port 44. In operation, this vent port 44 allows the compressed gas to escape from the cap 12 into the environment, instead of being communicated into the bottle 14, until it is plugged, such as by the finger of the user, at which point the compressed gas flows into the bottle 14 and drives the aqueous solution through the cap 12, into the wound to be irrigated. Thus, the vent port 44 conveniently acts as an on/off mechanism for actuating the wound irrigation device 10. It should be noted that the presence of bubbles in the aqueous solution indicates the flow of compressed gas into the bottle.

The outlet port 40 is coupled to a flexible or rigid tube 48 that extends into the bottle 14 and the aqueous solution, and may terminate in a backflow prevention valve 50 for preventing backflow of the compressed gas and/or aqueous solution from the bottle 14 into the flexible tubing 32 and compressed gas source 30. This backflow prevention valve 50 may consist of a check valve, a ball valve, a duck bill valve, or any other one-way valve mechanism, well known to those of ordinary skill in the art and are widely used in the healthcare industry. The force of the compressed gas, when directed down the flexible or rigid tube 48 easily overcomes the resistance of the backflow prevention valve 50 and pressurizes the irrigation solution. The flexible or rigid tube 48 may mate with the outlet port 40 via a positive sealing surface, a conical taper, or the like.

In operation, the vent port 44 is covered by the user with the bottle inverted and the protective rim 18 disposed about the wound to be irrigated. As a result, the aqueous solution is compressed, flows through the channels 22 manufactured into the longitudinal wall 20 of the cap 12 onto the wound, and exits the protective rim 18 via the one or more recesses 24, thereby irrigating the wound. The flow of compressed irrigation solution can be stopped by simply removing the finger from the vent port.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A wound irrigation device, comprising:
    a cap structure defined by a circumferential wall, a protective rim and a longitudinal wall, the cap structure configured to engage a bottle containing an irrigation solution at a first end;
    wherein the protective rim is disposed about a periphery of the cap structure at a second end opposite the first end, the protective rim extending upwardly from the longitudinal wall, wherein the protective rim is selectively disposed about or in proximity to a wound to be irrigated when in use;

wherein the circumferential wall extends downwardly from the longitudinal wall, such that the cap structure is defined into first and second chambers separated by the longitudinal wall;

one or more conduits for selectively communicating a compressed gas through the cap structure and into an interior of the bottle containing the irrigation solution to form a compressed irrigation solution; and wherein the longitudinal wall includes one or more channels extending therethrough for selectively communicating the compressed irrigation solution directly into the first chamber defined by the protective rim and to the wound to be irrigated.

2. The wound irrigation device of claim 1, further comprising a vent conduit in direct fluid communication with the one or more conduits for selectively venting the compressed gas through the cap structure and to an external environment.

3. The wound irrigation device of claim 2, wherein the vent conduit exits the cap structure coincident to one of a recess and a protrusion manufactured into an exterior surface of the cap structure.

4. The wound irrigation device of claim 1, further comprising a plurality of friction structures disposed about an external surface of the circumferential wall structure.

5. The wound irrigation device of claim 1, wherein the protective rim defines one or more recesses along an outer edge thereof through which the fluids and/or solids egress.

6. The wound irrigation device of claim 1, further comprising one or more backflow prevention valves disposed along the one or more conduits.

7. The wound irrigation device of claim 1, further comprising a flow regulator disposed along the one or more conduits.

8. The wound irrigation device of claim 1, wherein the one or more conduits are selectively coupled to a compressed gas source.

9. The wound irrigation device of claim 1, wherein the cap structure comprises one or more of threads and an elastomeric gasket disposed within its interior for engaging the bottle.

10. A method for using a wound irrigation device, comprising:

attaching a wound irrigation device to a bottle containing an irrigation solution, the wound irrigation device comprising:

a cap structure configured to engage the bottle containing the irrigation solution at a first end;

a protective rim disposed about a periphery of the cap structure at a second end opposite the first end, wherein the protective rim is selectively disposed about or in proximity to a wound to be irrigated when in use;

one or more conduits for selectively communicating a compressed gas through the cap structure and into an interior of the bottle containing the irrigation solution to form a compressed irrigation solution; and a longitudinal wall structure disposed within the cap structure and defining one or more channels there through for selectively communicating the compressed irrigation solution through the cap structure and to the wound to be irrigated;

coupling the one or more conduits of the wound irrigation device to a compressed gas source;

inverting the bottle containing the irrigation solution over the wound to be irrigated with the protective rim one of in contact with and at a predetermined distance from the wound to be irrigated; and actuating the wound irrigation device by obstructing a vent conduit in fluid communication with the one or more conduits such that the compressed gas flows into the bottle containing the irrigation solution and forces irrigation solution onto the wound to be irrigated through the one or more channels, the vent conduit selectively venting the compressed gas through the cap structure and to an external environment.

11. The method of claim 10, wherein the vent conduit exits the cap structure coincident to one of a recess and a protrusion manufactured into an exterior surface of the cap structure.

12. The method of claim 10, wherein the cap structure comprises a circumferential wall structure disposed about the longitudinal wall structure.

13. The method of claim 12, wherein the cap structure further comprises a plurality of friction structures disposed about an external surface of the circumferential wall structure.

14. The method of claim 10, wherein the protective rim defines one or more recesses along an outer edge thereof through which fluids and/or solids egress.

15. The method of claim 10, wherein the wound irrigation device further comprises one or more backflow prevention valves disposed along the one or more conduits, the backflow prevention valve preventing backflow.

16. The method of claim 10, wherein the wound irrigation device further comprises a flow regulator disposed along the one or more conduits that regulates fluid flow through the conduit.

17. The method of claim 10, wherein the cap structure comprises one or more of threads and an elastomeric gasket disposed within its interior for engaging the bottle.

18. A wound irrigation device, comprising:

a cap structure configured to engage a bottle containing an irrigation solution at a first end;

a protective rim disposed about a periphery of the cap structure at a second end opposite the first end, wherein the protective rim is selectively disposed about or in proximity to a wound to be irrigated when in use;

one or more conduits for selectively communicating a compressed gas through the cap structure and into an interior of the bottle containing the irrigation solution to form a compressed irrigation solution;

a longitudinal wall structure disposed within the cap structure and defining one or more channels there through for selectively communicating the compressed irrigation solution through the cap structure and to the wound to be irrigated; and a vent conduit in fluid communication with the one or more conduits for selectively venting the compressed gas through the cap structure and to an external environment, the vent conduit exiting the cap structure coincident to one of a recess and a protrusion manufactured into an exterior surface of the cap structure.

* * * * *